(12) United States Patent
Tang et al.

(10) Patent No.: US 12,023,387 B2
(45) Date of Patent: Jul. 2, 2024

(54) NIR-II EMISSIVE LUMINOGENS

(71) Applicants: THE HONG KONG UNIVERSTIY OF SCIENCE AND TECHNOLOGY, Hong Kong (CN); HKUST SHENZHEN RESEARCH INSTITUTE, Shenzhen (CN)

(72) Inventors: Benzhong Tang, Hong Kong (CN); Pengfei Zhang, Hong Kong (CN); Jen-Shyang Ni, Shenzhen (CN)

(73) Assignees: THE HONG KONG UNIVERSITY OF SCIENCE AND TECHNOLOGY, Hong Kong (CN); HKUST SHENZHEN RESEARCH INSTITUTE, Shenzhen (CN)

( * ) Notice: Subject to any disclaimer, the term of this patent is extended or adjusted under 35 U.S.C. 154(b) by 846 days.

(21) Appl. No.: 17/251,961

(22) PCT Filed: Jun. 14, 2019

(86) PCT No.: PCT/CN2019/091281
§ 371 (c)(1),
(2) Date: Dec. 14, 2020

(87) PCT Pub. No.: WO2019/238121
PCT Pub. Date: Dec. 19, 2019

(65) Prior Publication Data
US 2021/0260221 A1  Aug. 26, 2021

Related U.S. Application Data

(60) Provisional application No. 62/763,398, filed on Jun. 15, 2018.

(51) Int. Cl.
| | | |
|---|---|---|
| *A61K 49/00* | (2006.01) | |
| *A61B 5/00* | (2006.01) | |
| *A61K 41/00* | (2020.01) | |
| *C07D 309/34* | (2006.01) | |
| *G01N 21/64* | (2006.01) | |
| *A61N 5/06* | (2006.01) | |

(52) U.S. Cl.
CPC ...... *A61K 49/0021* (2013.01); *A61K 41/0057* (2013.01); *C07D 309/34* (2013.01); *G01N 21/6428* (2013.01); *G01N 21/6456* (2013.01); *A61B 5/0071* (2013.01); *A61N 5/062* (2013.01); *G01N 2021/6439* (2013.01)

(58) Field of Classification Search
CPC .... A61K 49/00; A61K 49/0021; A61K 31/00; A61K 31/351; A61K 41/00; A61K 41/0057; C07D 309/34; C07D 309/32; G01N 2021/6439; G01N 21/6456; G01N 21/6428; A61B 5/0071; A61N 5/062
USPC ... 424/1.11, 1.65, 9.1, 9.2, 9.3, 9.4, 9.5, 9.6, 424/1.49; 549/356
See application file for complete search history.

(56) References Cited

U.S. PATENT DOCUMENTS 5,306,587 A * 4/1994 Terrell ................ G03G 5/0629
430/72

FOREIGN PATENT DOCUMENTS

| EP | 0384040 A1 | 8/1990 |
| JP | H0445435 A | 2/1992 |
| KR | 101294800 B1 | 8/2013 |

OTHER PUBLICATIONS

Bespalov et al., Scientific-Research of Organic Intermediates and Dyes, Moscow. Translated from Khimiya Geterotsiklichskikh Soedinenii, No. 5, pp. 603-608. (Year: 1985).*

* cited by examiner

*Primary Examiner* — D. L. Jones
(74) *Attorney, Agent, or Firm* — Nath, Goldberg & Meyer; Joshua B. Goldberg

(57) ABSTRACT

Small molecule compounds having aggregation-induced emission (AIE) characteristics include donor-acceptor (D-A) structural NIR fluorophores based on 1,3-bis(dicyanomethylene)indan (BDCI), a strong and steric electron-deficient acceptor. A twisted quasi-double bond (TQDB) links each electron donor with the acceptor. The compounds can be used as NIR-II fluorescent dyes for in vivo imaging. The compounds can conjugate with bioactive molecules, such as peptides, sugars, aptamers and antibodies, to provide specific and active NIR-II fluorescent probes. The compounds can serve as active NIR-II fluorescent probes in many applications, such as, cancer cell-targeted imaging, accurate diagnosis of disease, and image-guided phototherapy.

18 Claims, 5 Drawing Sheets

HRMS (MALDI-TOF; m/z, [M]+)
Calcd: 858.3107
Found: 858.3108

Fig. 6
| Fig. 7A | Fig. 7B | Fig. 7C | Fig. 7D | Fig. 7E | Fig. 7F |
|---|---|---|---|---|---|
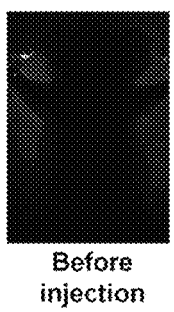 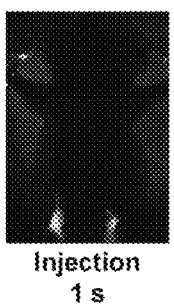 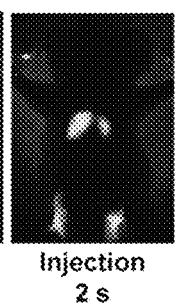 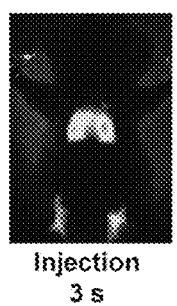 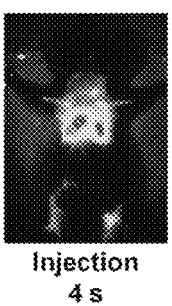 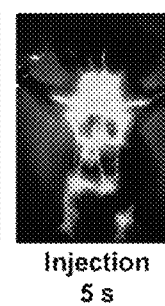 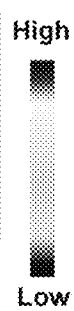
| Before injection | Injection 1 s | Injection 2 s | Injection 3 s | Injection 4 s | Injection 5 s |
|---|---|---|---|---|---|

NIR-II EMISSIVE LUMINOGENS

FIELD

The present subject matter relates generally to a series of compounds capable of aggregation-induced emission in the spectrum range of 900 nm-1700 nm and their application in in vivo imaging.

BACKGROUND

Organic dyes with NIR emission are favorable in many fields, such as organic light-emitting diode (OLED), fluorescent imaging, and anti-counterfeit technology. Near-infrared (NIR) fluorescence imaging is a biocompatible imaging technology that can realize noninvasive, high resolution, and real time visualization as well as dynamic tracking of a living organism at the cellular level. As such, NIR fluorescence imaging shows great potential in early detection and accurate diagnosis of disease.

In comparison with other imaging techniques, such as computed tomography (CT), magnetic resonance imaging (MRI), and positron emission tomography (PET), fluorescence imaging has the advantages of low cost, high resolution, and real-time monitoring ability. Due to minimal photon scattering and negligible tissue auto-fluorescence in the spectrum range of 1000-1700 nm (the second near-infrared widow, "NIR-II"), NIR-II fluorescence imaging provides improved imaging performance with higher image contrast at much greater penetration depth compared to conventional fluorescence imaging using NIR-I fluorescent light (first near-infrared window within a spectrum range of 650-900 nm).

A large variety of fluorescent materials including natural polymers, organic small molecular dyes, inorganic quantum dots, and organic fluorescent nanoparticles have been investigated for fluorescence imaging and sensing. Among them, fluorescent nanoparticles based on organic dyes have been a research focus due to their tunable size, low cytotoxicity, good photostability, and surface functionalization feasibility.

Organic emitters are rich in variety. The traditional planar organic dyes, however, provide weakened or even quenched emission in aggregate, known as the notorious aggregation-caused quenching (ACQ). As such, application of the traditional planar organic dyes is greatly restricted. The ACQ phenomenon is particularly significant for dyes with red or near-infrared red (NIR) emission, since their elongated π-conjugation or strong donor-acceptor (D-A) interaction favor strong π-π interaction to quench the emission. In contrast to the ACQ system, a novel class of molecular rotors discovered by Tang et al. exhibit aggregation-induced emission (AIE), which means they exhibit little or no emission in dilute solution, but enhanced fluorescence in the aggregate through restriction of intramolecular motion (RIM). The unique emission property of AIE luminogens (AIEgens) paved the way for preparation of highly emissive organic fluorescence nanoparticles.

Organic dyes with NIR absorbance and emission are more favorable compared to other traditional visible-light emissive dyes in bio-application due to their lower cellular or tissue auto-fluorescence interference and anti-photo bleaching ability. Many NIR fluorophores are toxic, however. In addition, many existing NIR-II fluorophores are emissive in both the separate and aggregate states. The "always-on" feature of these NIR-II fluorophores provide limited responsive ability to fluctuations of microenvironments in vivo.

Synthesis of existing NIR fluorophores is often complex. A rational design and synthesis method for NIR-II emissive AIEgens with NIR absorbance was previously difficult to achieve. First, because most AIEgens have highly twisted structures, it is very difficult to effectively red-shift the emission by merely expanding the electron delocalization of π-system due to the poor π-conjugation of the molecular backbone. Second, excessively large π-conjugation through fused rings or double bonds likely leads to poor solubility, increased instability of the AIEgens, and/or the ACQ problem. Constructing D-A (donor-acceptor) structures is a very efficient strategy for affording red emitters. However, the twisted structures of some fluorophores cause emission of D-A type AIEgens to suffer from the influence of twisted intramolecular charge transfer (TICT), which has been proposed as one of the major non-radiative decay pathways for D-A type fluorophores. Additionally, expanding the π-conjugation of D-A structures likely results in the ACQ problem, due to the strong intermolecular π-π interaction.

Accordingly, organic luminogens having a D-A structure which nevertheless overcome these challenges are highly desirable.

SUMMARY

The present subject matter contemplates small molecule compounds having aggregation-induced emission (AIE) characteristics. The present compounds include donor-acceptor (D-A) structural NIR fluorophores based on 1,3-bis(dicyanomethylene)indan (BDCI), a strong and steric electron-deficient acceptor. An electron donor is linked to the acceptor by a twisted quasi-double bond (TQDB). It is believed that the AIE characteristics of the present compounds stem, at least partially, from the presence of the twisted quasi-double bonds.

The compounds can provide emission in the second near-infrared window (NIR-II) and, thereby, serve as NIR-II activated fluorescent probes. The compounds are non-toxic and can be used as NIR-II fluorescent dyes for in vivo imaging. The compounds can conjugate with bioactive molecules, such as peptides, sugars, aptamers and antibodies, to provide specific and active NIR-II fluorescent probes. The compounds can serve as active NIR-II fluorescent probes in many applications, such as, cancer cell-targeted imaging, accurate diagnosis of disease, and image-guided phototherapy. Since the present compounds are useful for imaging in the NIR-II window, they can be used for deep-tissue, high resolution optical imaging in vivo.

In an embodiment, the compounds can have the following backbone structural formula:

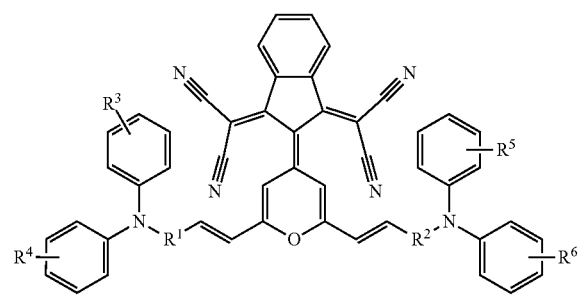

wherein each of $R_1$ and $R_2$ is independently selected from the group consisting of

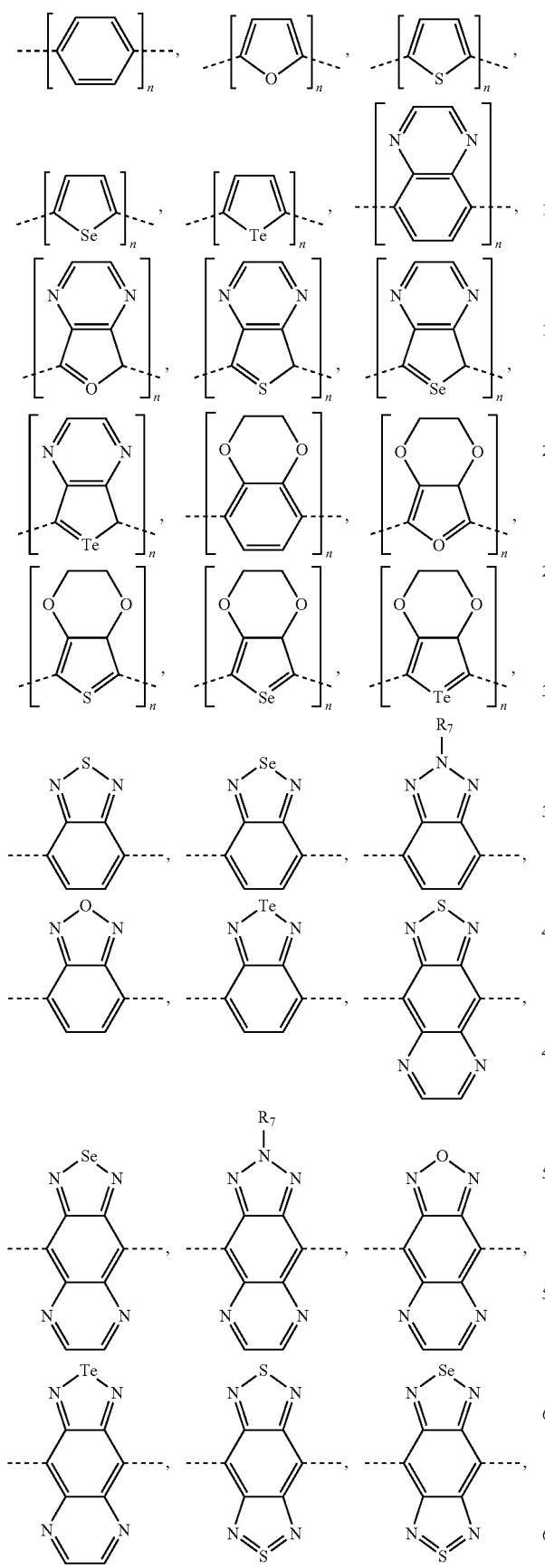

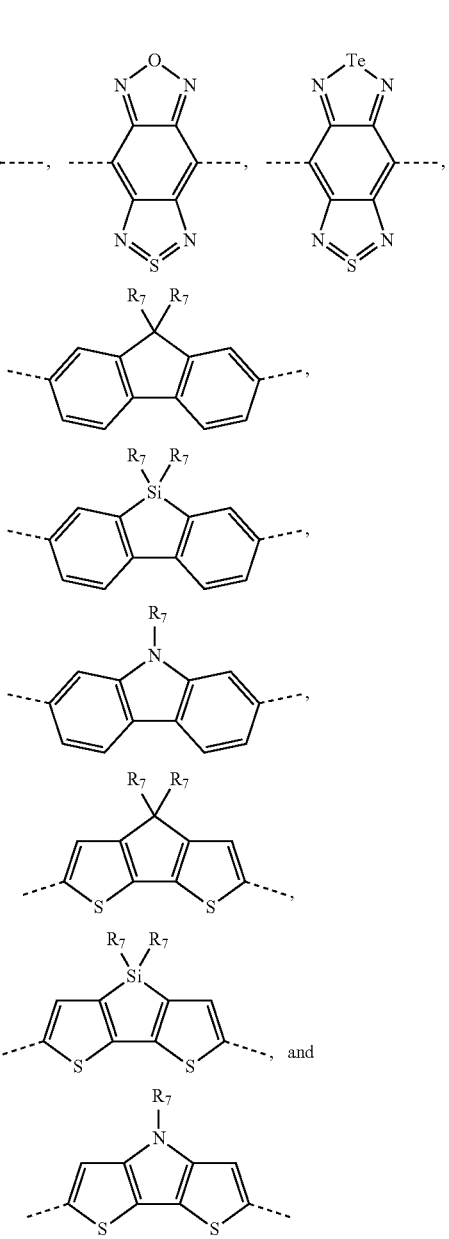

wherein each of $R_3$, $R_4$, $R_5$, and $R_6$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein $R_7$ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and wherein n is an integer selected from 1, 2, 3, 4, and 5.

In an embodiment, each of $R_1$ and $R_2$ can be.

In an embodiment, each of $R_3$, $R_4$, $R_5$, and $R_6$ can be hydrogen.

In an embodiment, n is 1.

In a further embodiment, the compound is

TSPCI

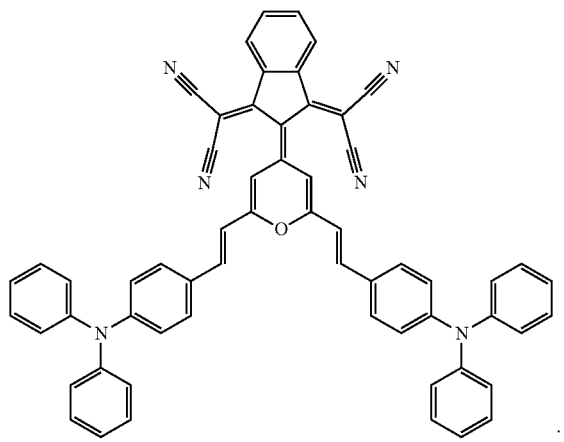

BRIEF DESCRIPTION OF DRAWINGS

Various embodiments will now be described in detail with reference to the accompanying drawings.

FIG. 6 depicts the spatial resolution anlaysis, in order, of each of the NIR-II fluorescence images provided in FIGS. 5A-5J.

FIG. 7 depicts time course NIR-II fluorescence images of a nude mouse (A) before intravenous injection of TSPCI solution; (B) one second after injection of TSPCI solution; (C) two seconds after injection of TSPCI solution; (D) three seconds after injection of TSPCI solution; (E) four seconds after injection of TSPCI solution; and (F) five seconds after injection of TSPCI solution.

DETAILED DESCRIPTION

Definitions

Figure 1:
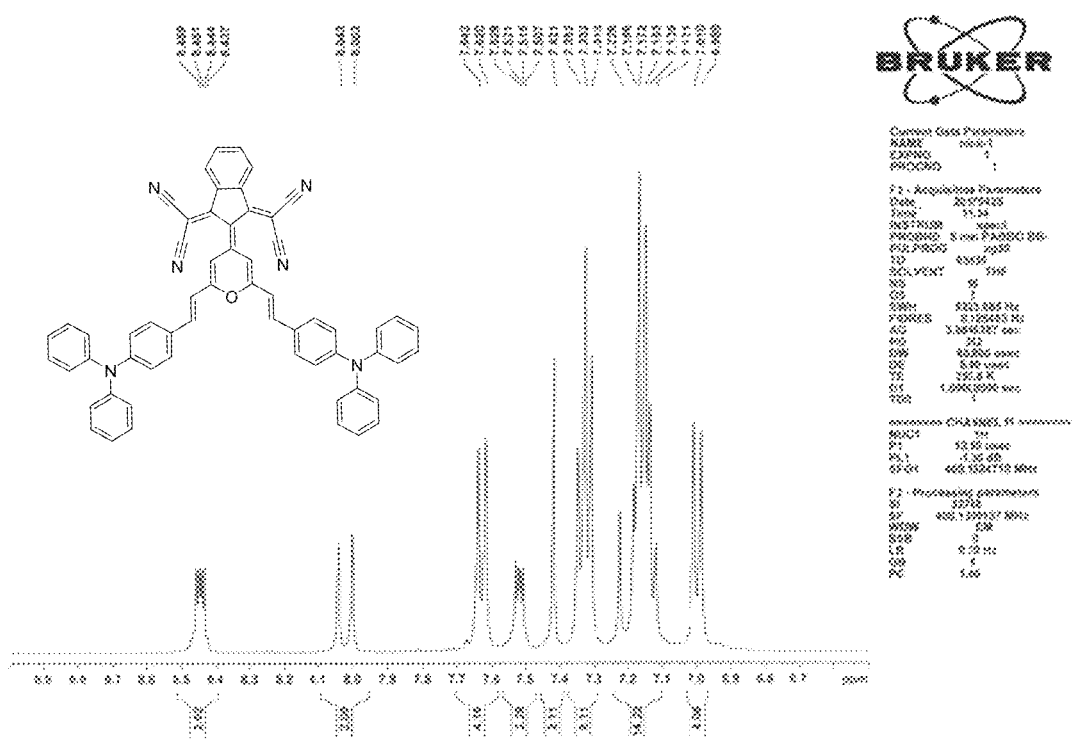
FIG. 1 depicts the 1H NMR spectra of TSPCI.
Figure 2:
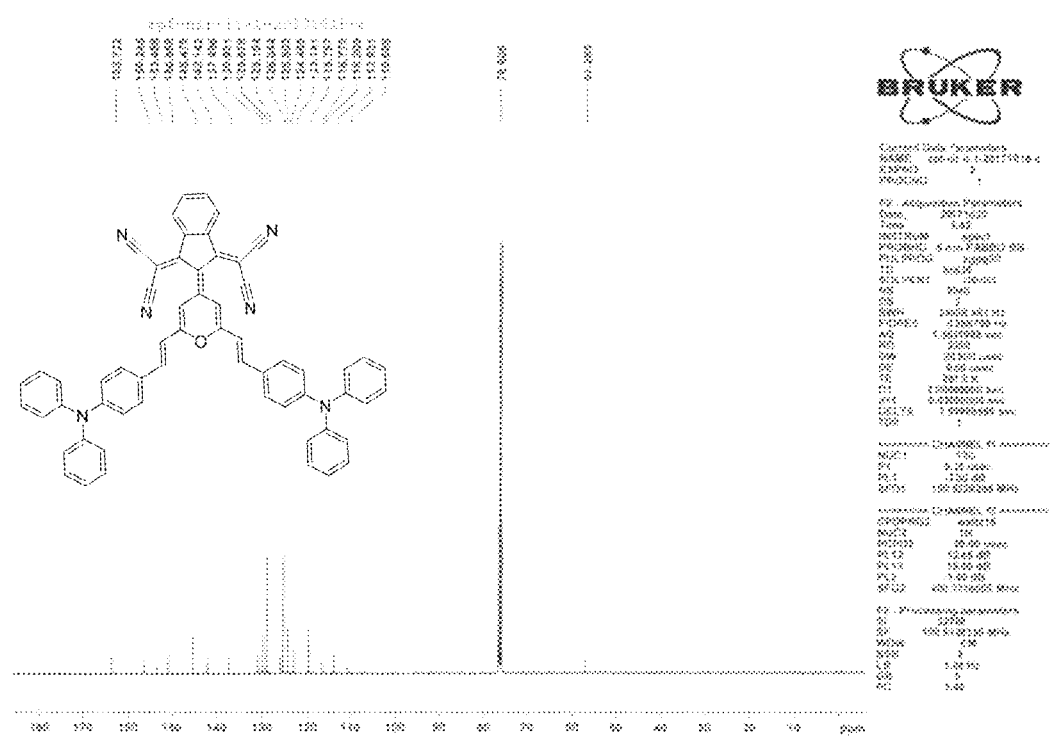
FIG. 2 depicts the 13C NMR spectra of TSPCI.
Figure 3:
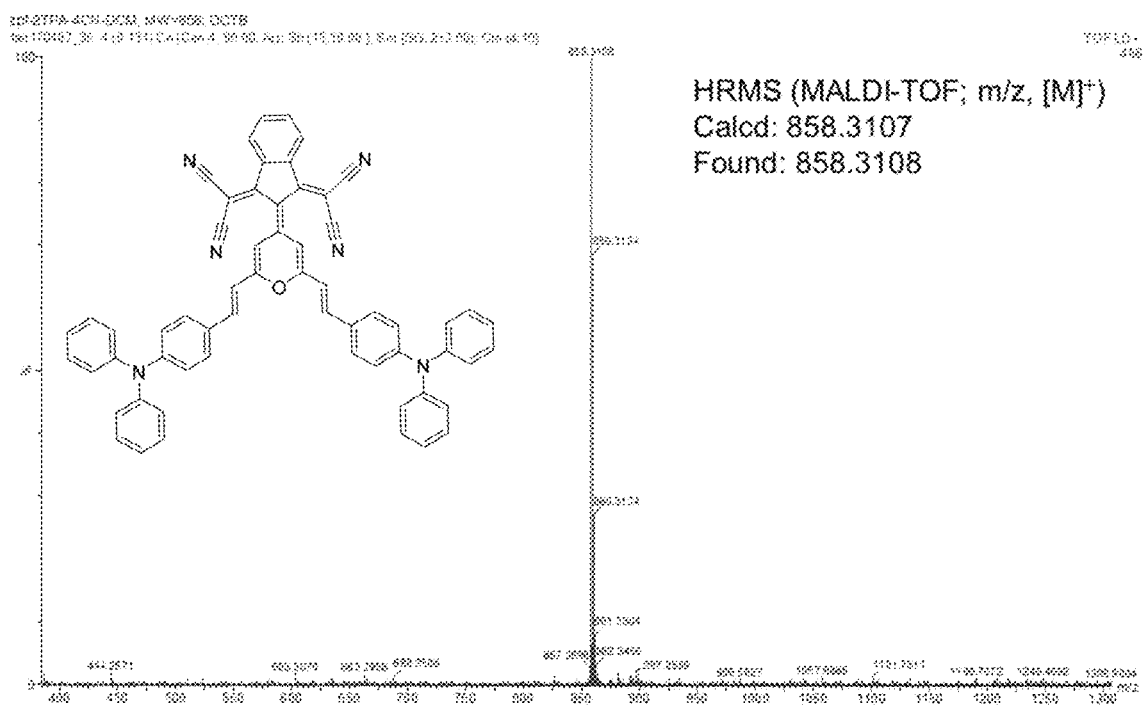
FIG. 3 depicts a high resolution mass spectrum (MALDI-TOF) of TSPCI.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

The term "$\lambda_{ex}$" as used herein refers to excitation wavelength.

The phrase "aggregation caused quenching" or "ACQ" as used herein refers to the phenomenon wherein the aggregation of n-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refer to a molecule which exhibits fluorescence; "luminogen" or "luminophore" as used herein refer to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, IH-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Compounds

The present compounds can include a donor-acceptor (D-A) structure in which a twisted quasi-double bond (TQDB) links an electron-deficient acceptor group to an electron donor group.

An exemplary electron-deficient acceptor can include 1,3-bis(dicyanomethylene)indan (BDCI) based compounds, having the following structural formula
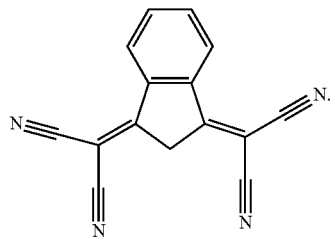
BDCI
An exemplary electron donor can include at least one compound selected from
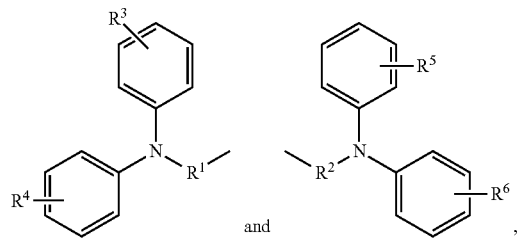
and
wherein each of $R_1$ and $R_2$ is independently selected from the group consisting of
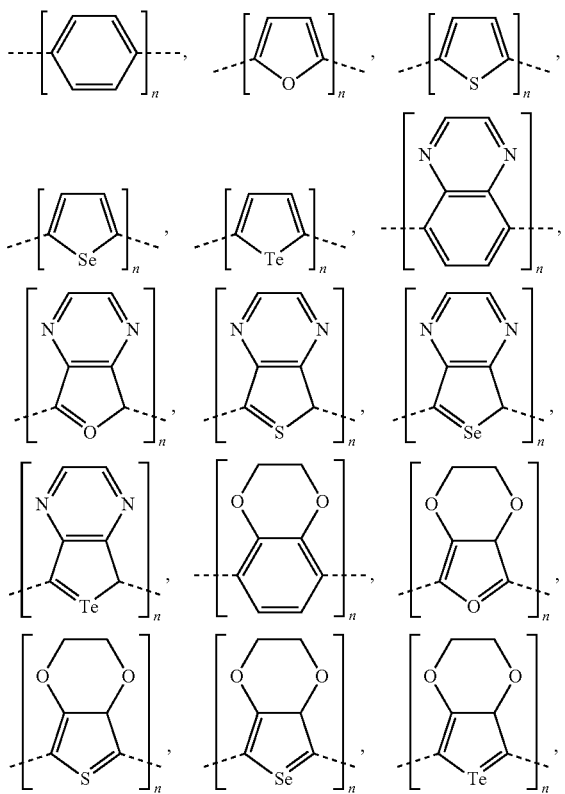
-continued
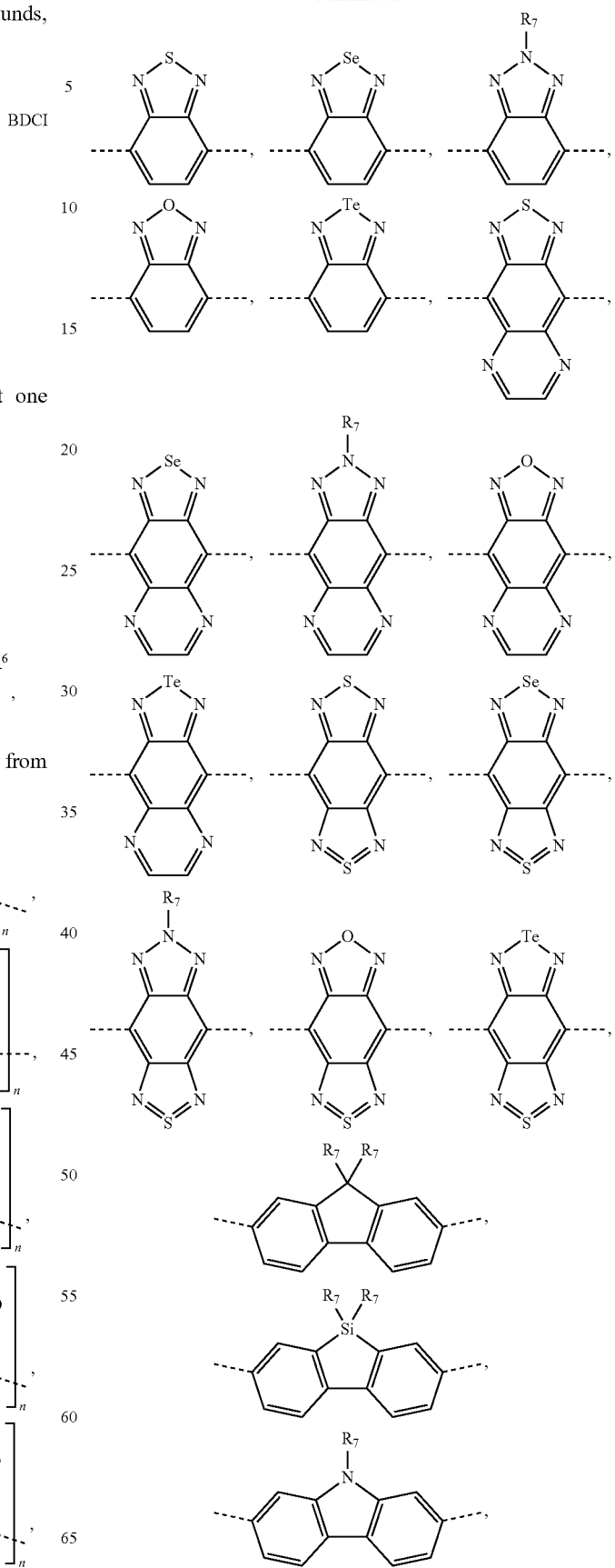

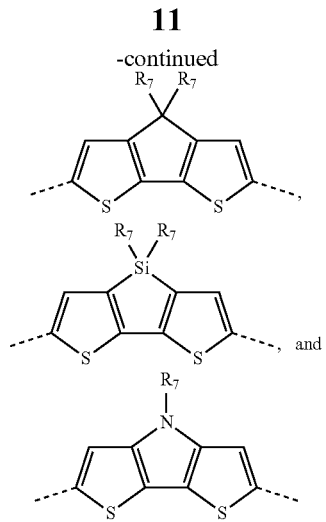

wherein each of $R_3$, $R_4$, $R_5$, and $R_6$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein $R_7$ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and n is an integer selected from 1, 2, 3, 4, and 5.

In an embodiment, an exemplary electron donor can have the following backbone structural formula

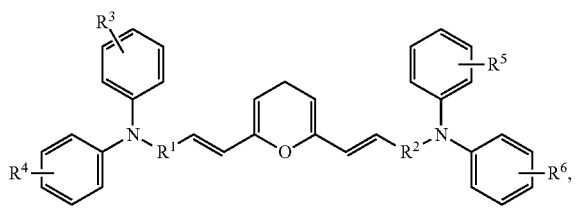

wherein each of $R_1$ and $R_2$ is independently selected from the group consisting of

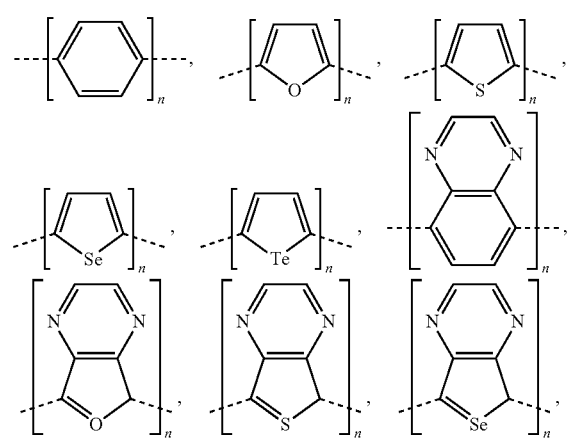

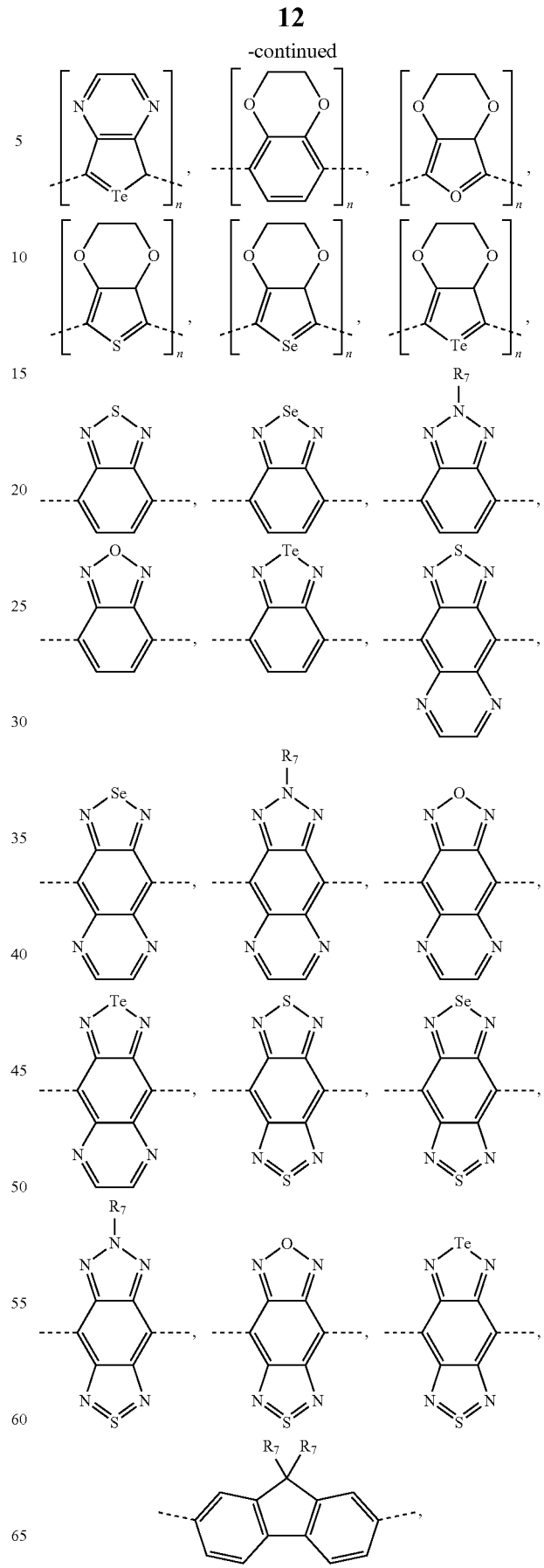

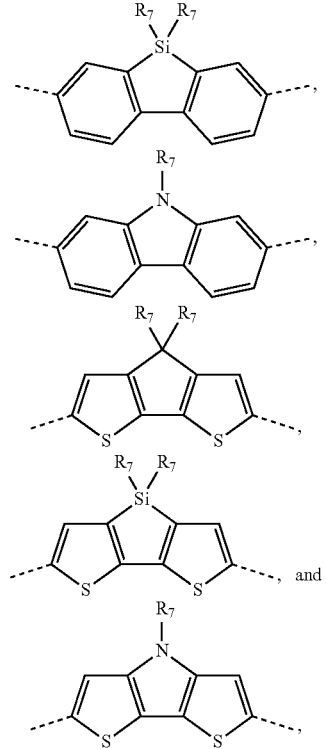

wherein each of $R_3$, $R_4$, $R_5$, and $R_6$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein $R_7$ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and n is an integer selected from 1, 2, 3, 4, and 5.

According to an embodiment, the present subject matter relates to compounds having the following backbone structural formula

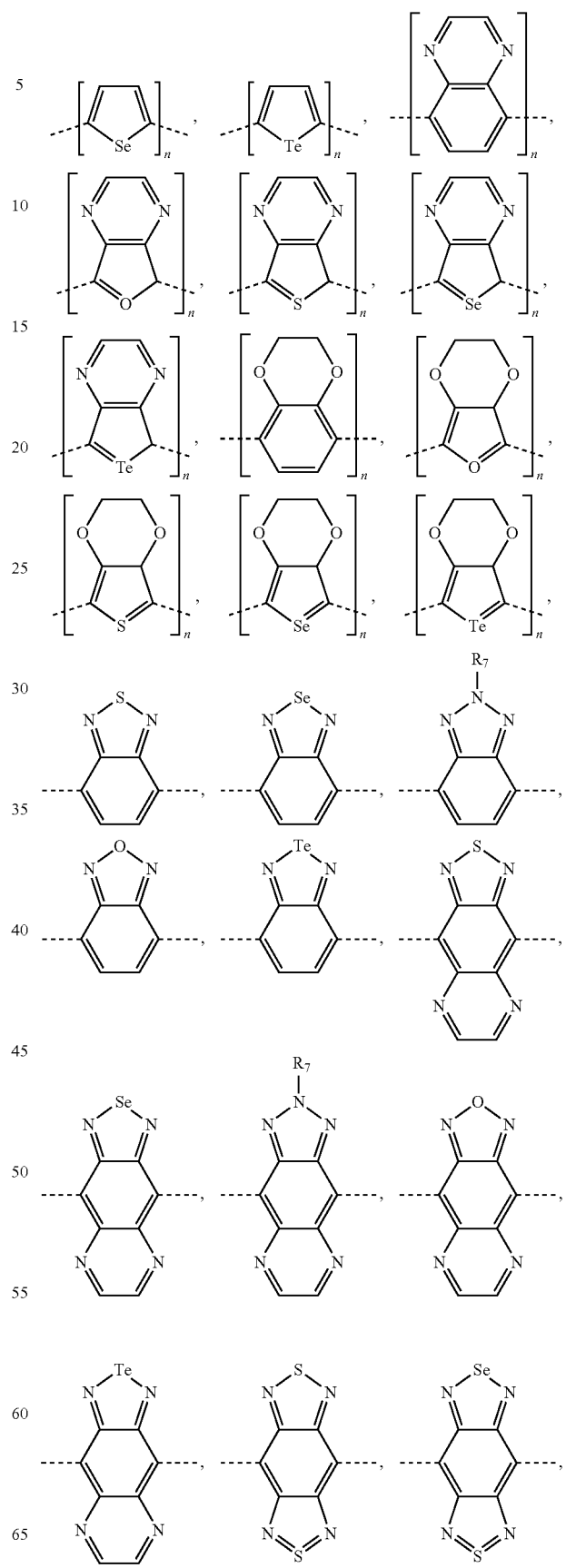

wherein each of $R_1$ and $R_2$ is independently selected from

-continued

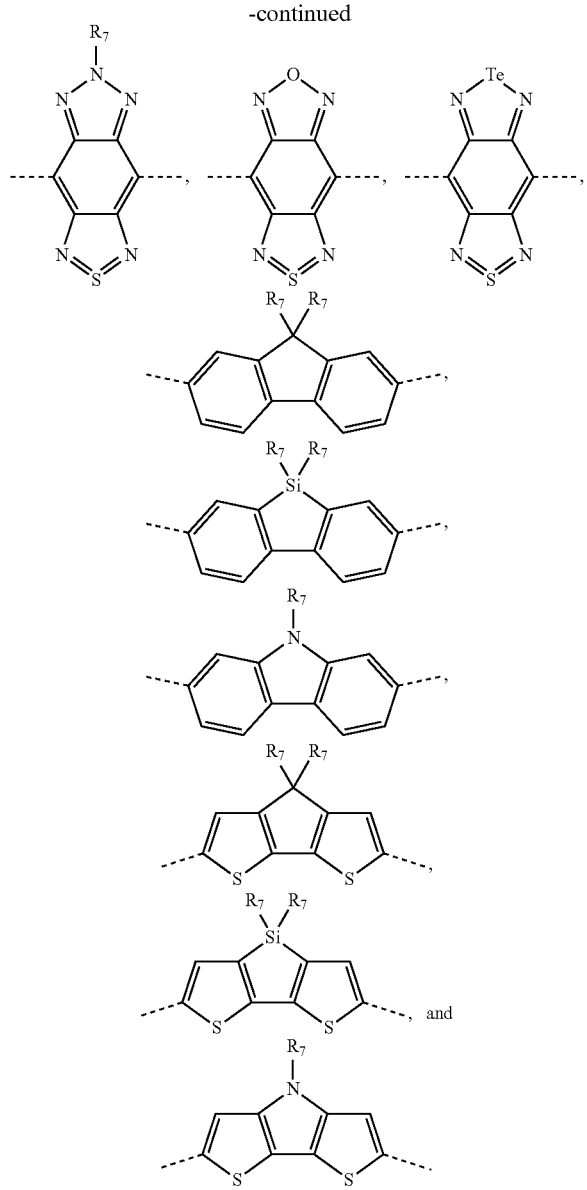

wherein each of $R_3$, $R_4$, $R_5$, and $R_6$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein $R_7$ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and n is an integer selected from 1, 2, 3, 4, and 5.

In an embodiment, each of $R_1$ and $R_2$ can be

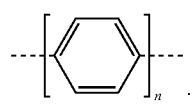

In an embodiment, each of $R_3$, $R_4$, $R_5$, and $R_6$ can be hydrogen.

In an embodiment, n can be 1.

In a further embodiment, the compound is "TSPCI," having the following structure

TSPCI

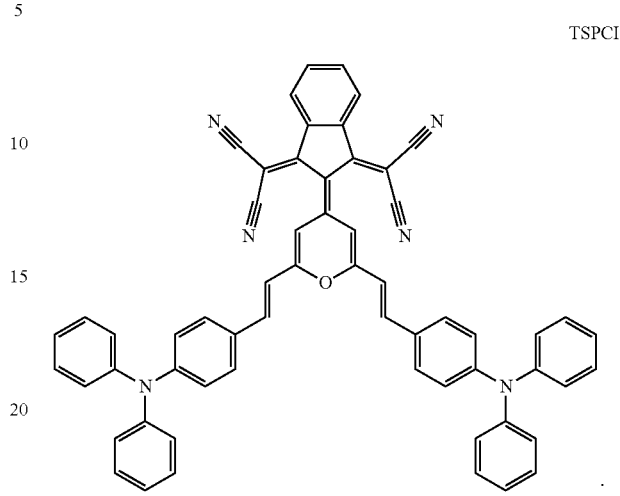

Compound Properties

The present compounds have fluorescent properties when in a solid state. For example, the present compounds can provide ~35-fold higher signal enhancement from solution state to aggregate state and wide absorption (500 nm-850 nm).

The present compounds can be used as a probe in imaging methods. The imaging methods can include, for example, fluorescence imaging in the near infrared spectral range of 900 nm to 1700 nm. For example, the compounds can exhibit bright emission in the NIR-II spectral range of 1000 nm to 1700 nm, or in certain more limited ranges therein, such as 1000 nm to 1300 nm. By virtue of their emission in the NIR-II spectrum, the present compounds provide a high signal to noise ratio. A fluorescence imaging method can include contacting a target cell with one or more of the present compounds and conducting fluorescence imaging of the contacted target cell in the near infrared spectral region.

The present compounds can exhibit excellent AIE properties and can be easily synthesized from commercially available raw materials. The present compounds can be used in cellular imaging methods to detect the presence or absence of a target of interest in a target cell. A target cell can be contacted with one or more of the present compounds. The presence or absence of the target of interest can be detected using an imaging method. The target of interest can include at least one of a peptide, a sugar, an aptamer, and an antibody. The target cell can be a cancer cell, for example.

In an embodiment, a method of killing a target cancer cell can include contacting the target cancer cell with one or more of the present compounds, imaging the target cancer cell while the compound contacts the target cancer cell, irradiating the target cancer cell with light while the compound is contacting the target cancer cell to kill the target cancer cell.

Accordingly, the present compounds can have various applications, including cancer cell targeted imaging, disease diagnosis and image-guided phototherapy. According to an embodiment, the present compounds can be useful in technologies relating to the military, energy, and the environment. For example, the present compounds can have applications in night vision, solar energy, and desalination technologies.

AIE Activity

The present subject matter contemplates organic compounds having aggregation-induced emission (AIE) characteristics. The compounds can possess fluorescence properties in the solid or aggregate state. In the solution state, the compounds are less emissive.

An exemplary compound according to the present teachings is TSPCI. As described in detail herein, TSPCI is less emissive in the solution state. In the aggregate state, however, the emission of this compound is induced or rejuvenated by the restriction of intramolecular motions (RIM)

Method of Synthesis

The present compounds can be synthesized using a two-step process: 1) reacting 1,3-bis(dicyanomethylene)indan (BDCI) with 2,6-dimethyl-4-pyrone (1) in acetic anhydride to yield an intermediate (SPCI); and 2) condensing the intermediate (SPCI) to provide the present compounds. An exemplary reaction scheme is provided below:

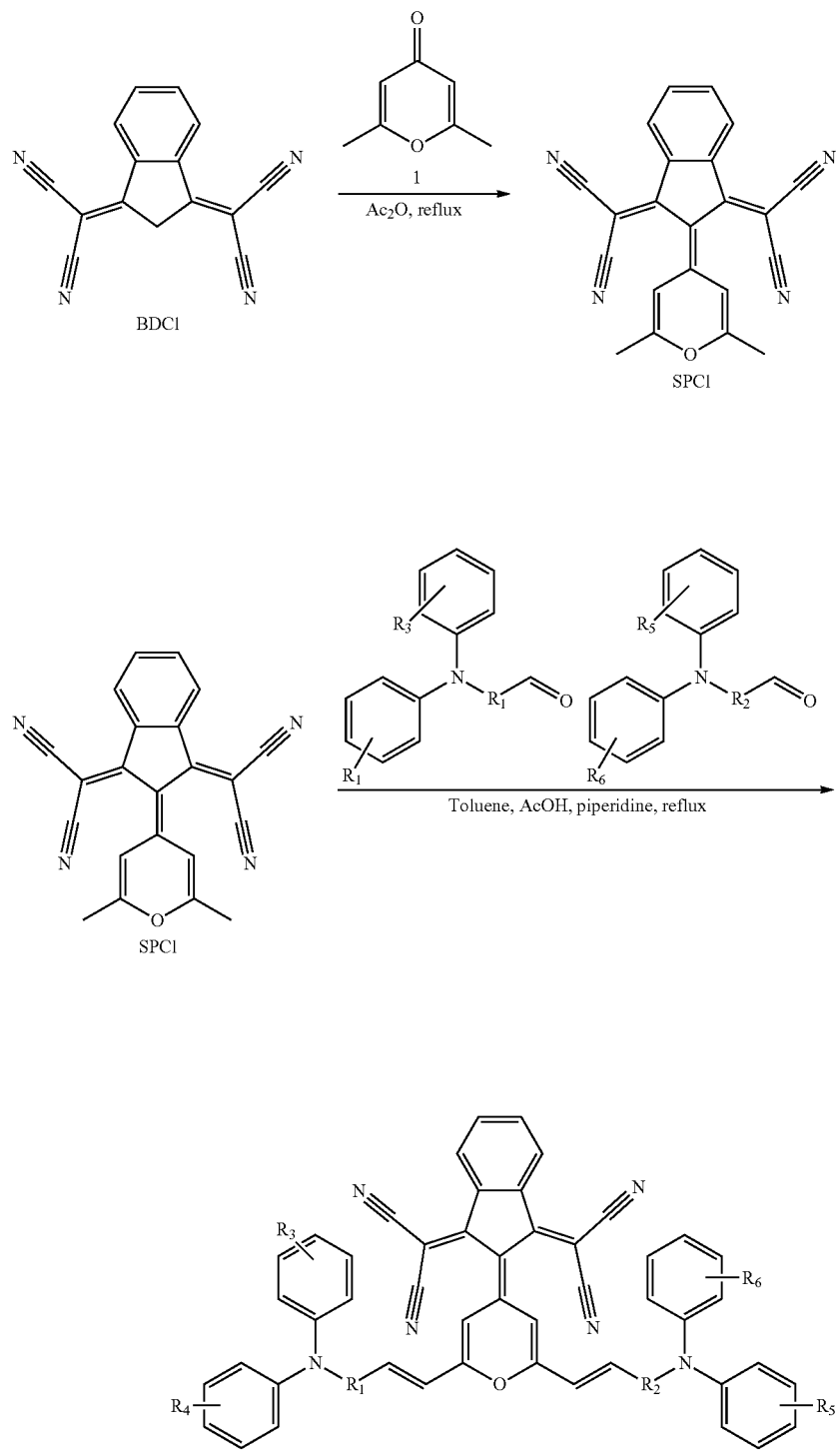

According to an embodiment, the present subject matter relates to a method of synthesizing a fluorescent compound with a twisted quasi-double bond bridging an electron-deficient acceptor and an electron donor, the method comprising:

reacting 1,3-bis(dicyanomethylene)indan with 2,6-dimethyl-4-pyrone to provide an intermediate compound (SPCI) having the following structural formula

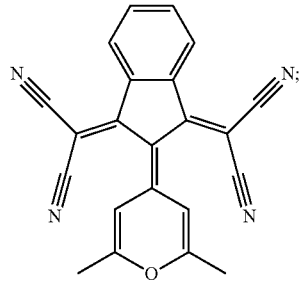

M1 and
reacting the intermediate compound with

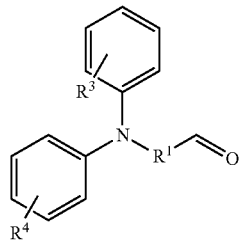

and

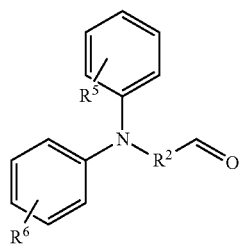

to provide the fluorescent compound,
wherein each of $R_1$ and $R_2$ is independently selected from the group consisting of

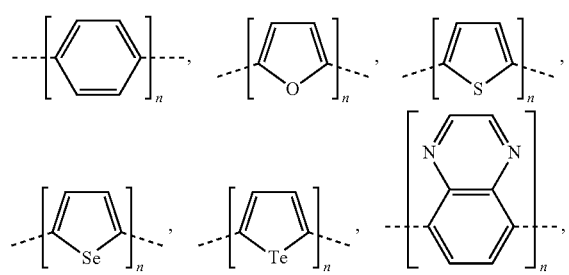

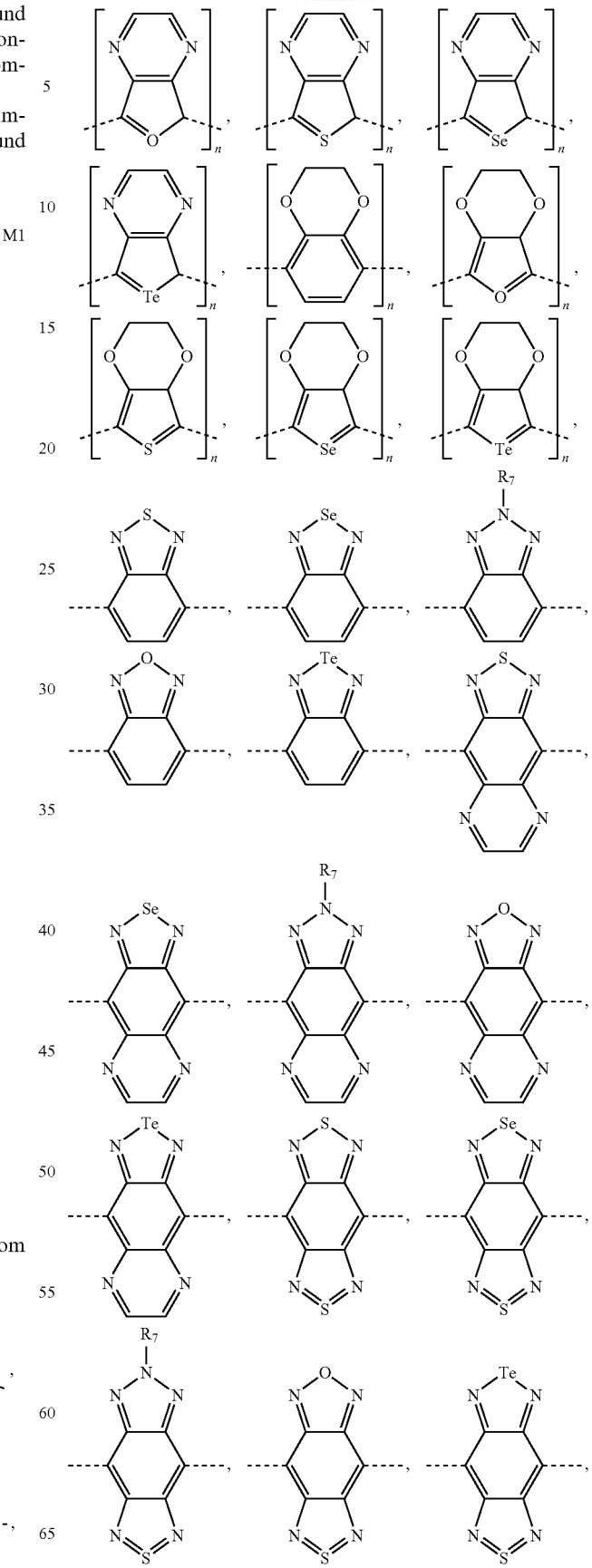

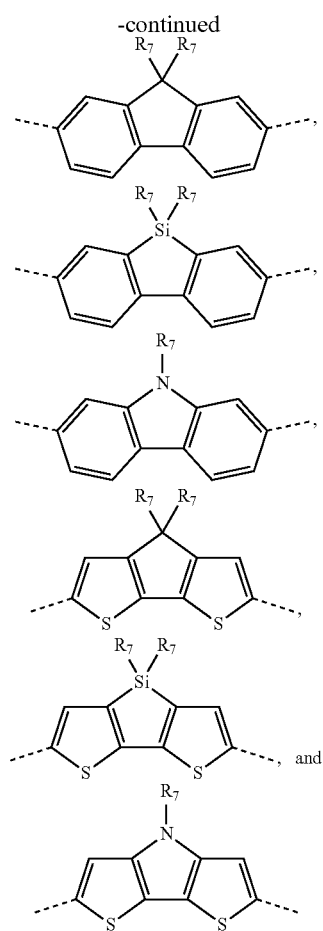

wherein each of R₃, R₄, R₅, and R₆ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein R₇ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and n is an integer selected from 1, 2, 3, 4, and 5.

The present teachings are illustrated by the following examples.

EXAMPLES

Example 1

Synthesis and Characterization of SPCI

In a 50 mL two-necked flask, a mixture of 1 (2,6-disubstituted y-pyrones, 300 mg, 2.41 mmole), BDCI (1,3-bis(dicyanomethylene) indan) (648 mg, 2.63 mmole), and acetic anhydride (10 ml, 97.8 mmole) was refluxed overnight. Then, the solution was cooled to room temperature and filtered to obtain the crude product, which was purified by silica column chromatography (eluent solvent, dichloromethane:hexane=1:1, V/V) to obtain compound SPCI as a purple powder (626 mg), yield 74%. ¹H NMR (400 MHZ, DMSO-d₆) δ: 8.34 (br, 2H), 7.87 (s, 2H), 7.68 (br, 2H), 2.81 (s, 6H). ¹³C NMR (100 MHz, CDCl₃) δ: 169.03, 158.11, 154.08, 137.53, 131.73, 123.57, 120.11, 115.56, 115.53, 110.58, 61.14, 20.49. HRMS (MALDI-TOF), m/z: [M]+ calculated: 348.1011, found: 348.1037.

Example 2

Synthesis and Characterization of TSPCI

An exemplary reaction scheme for preparing TSPCI is as provided below:

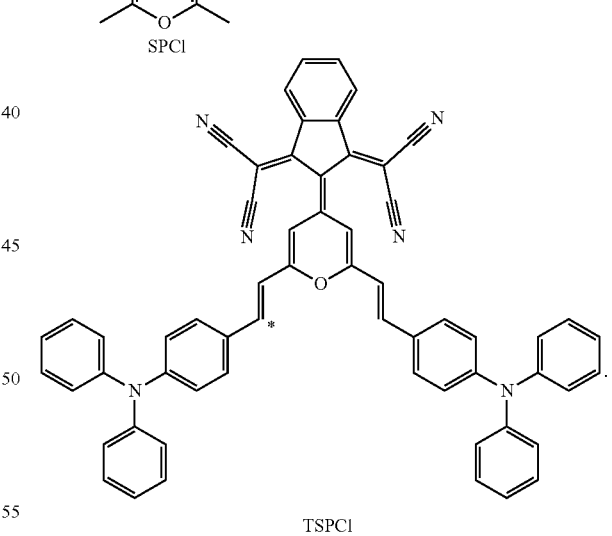

1,3-bis(dicyanomethylene)indan (BDCI) was reacted with 2,6-dimethyl-4-pyrone (1) in acetic anhydride at 120° C. to yield the intermediate, SPCI. In a 50 mL two-necked flask, SPCI (168 mg, 0.48 mmol) and 4 (4-(N, N-Diphenylamino) benzaldehyde (329 mg, 1.21 mmol) were dissolved in anhydrous toluene (15 mL) to provide a mixture. Then, piperidine (1.0 mL) and acetic acid (0.5 mL) were added to the aforementioned mixture. The solution was stirred and heated at 120°C for 8 h, while the solution color changed from purple to dark blue. Then, the solution was cooled to room temperature and filtered to obtain the crude product, which was purified by silica column chromatography (eluent solvent, dichloromethane:methanol=100:1, V/V) to obtain TSPCI as a black powder (46.5 mg) (FIG. 4A), yield 4%. $^1$H NMR (400 MHZ, THF-d8) δ: 8.44 (dd, J=3.2 Hz, J=6.0 Hz, 2H), 8.02 (d, J=16.0 Hz, 2H), 7.63 (d, J=8.8 Hz, 8H), 7.51 (dd, J=3.2 Hz, J=5.6 Hz, 2H), 7.35-7.31 (m, 8H), 7.22-7.12 (m, 14H), 6.99 (d, J=8.4 Hz, 2H). $^{13}$C NMR (100 MHZ, CDCl$_3$) δ: 163.72, 156.25, 153.49, 150.87, 145.48, 142.14, 137.50, 130.93, 129.88, 129.10, 126.04, 125.50, 124.47, 123.14, 119.79, 116.78, 116.21, 113.83, 110.69, 57.29. HRMS (MALDI-TOF), m/z: [M]+ calculated: 858.3107, found: 858.3108.

Example 3

Photophysical Properties of TSPCI

Figures 4A, 4B, 4C, 4D:
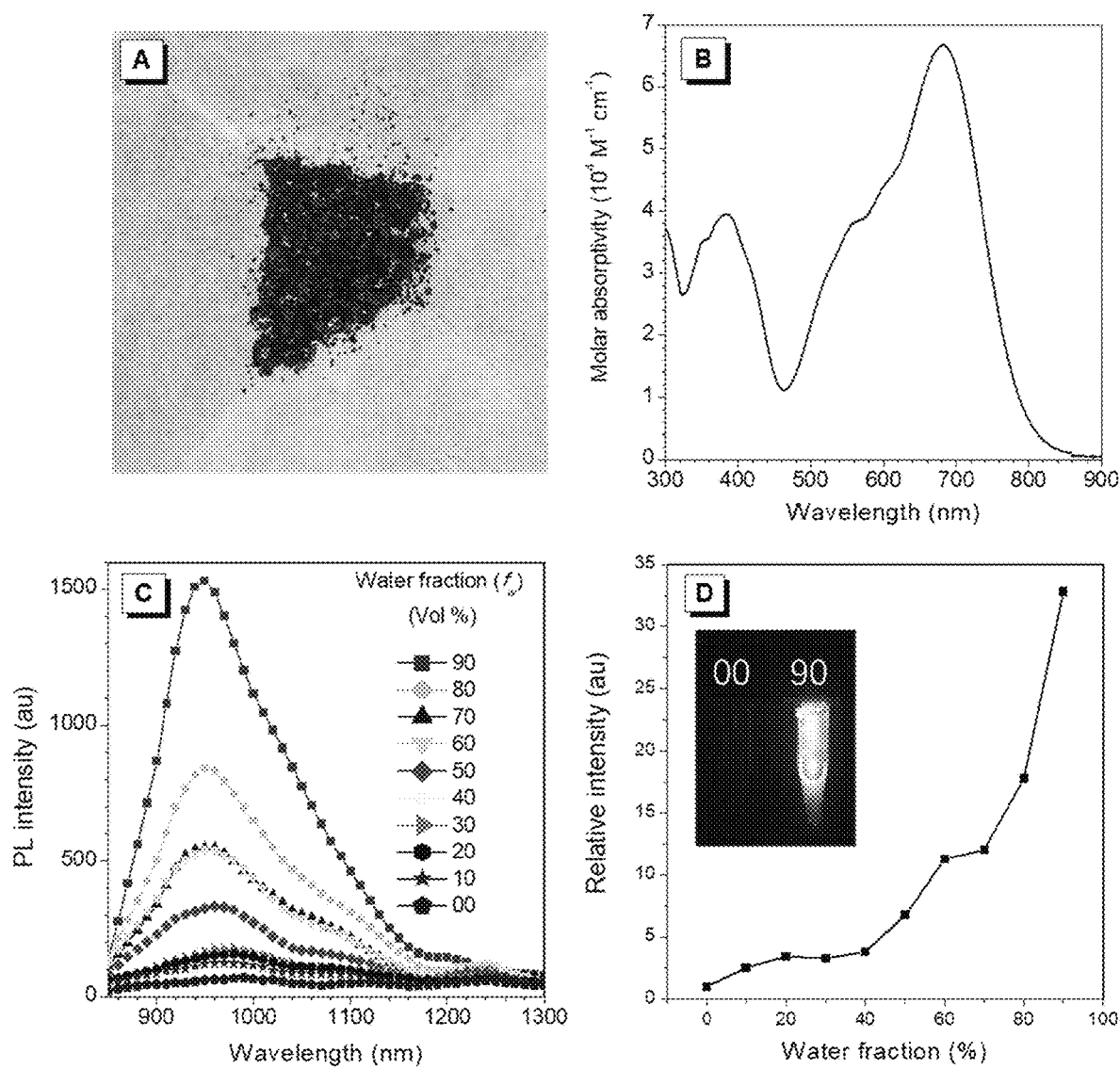
FIG. 4 depicts (A) an image of TSPCI powder in daylight; (B) the UV-vis absorption spectrum of TSPCI; (C) the photoluminescence (PL) spectra of TSPCI in THF and THF/water mixtures with different water fractions ($f_w$); and (D) the plot of relative PL intensities at 950 nm versus the $f_w$ (concentration: 10 μM; excitation wavelength: 808 nm). The inset of FIG. 4D shows fluorescence photographs of TSPCI in THF ($f_w$=0 vol %) (left) and water/THF mixture ($f_w$=90 vol %) (right) in 1.5 mL centrifuge tubes under laser illumination of 808 nm wavelength, which were collected using an InGaAs camera (1000-1600 nm).
Figure 5A:
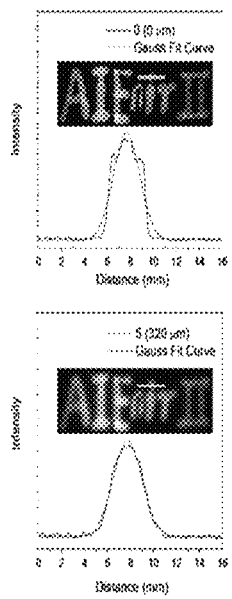
FIG. 5 depicts full width at half maximum (FWHM) curves analysis of a TSPCI-drawn panel (NIR-II fluorescence) with (A) no paper layer covering; (B) one paper layer (64 μm); (C) two paper layers (128 μm); (D) three paper layers (192 μm); (E) four paper layers (256 μm); (F) five paper layers (320 μm); (G) six paper layers (384 μm); (H) seven paper layers (448 μm); (I) eight paper layers (512 μm); and (J) nine paper layers (576 μm). The inset in each figure shows gray-scaled fluorescence images of the panels taken using an InGaAs-based NIR-II camera.
Figure 5B:
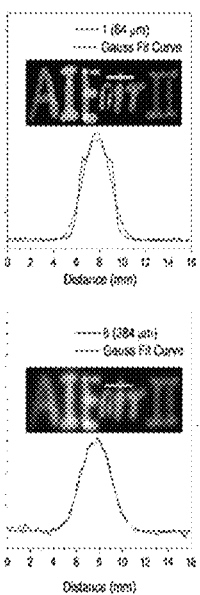
Figure 5C:
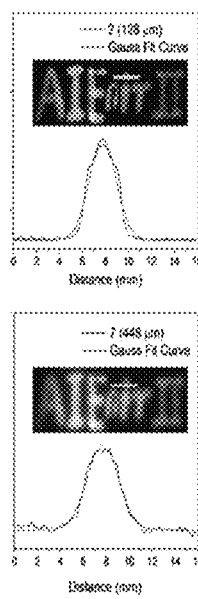
Figure 5D:
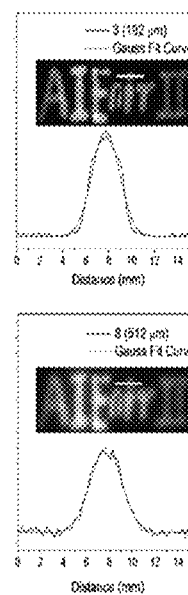

The UV-vis spectrum measured in THE solution (10 μM) showed the maximal absorption wavelength at 682 nm with a relatively high molar extinction coefficient (up to 6.67×104 M$^{-1}$ cm$^{-1}$) (FIG. 4B). The AIE property of TSPCI was investigated by varying the water fractions (fw) in tetrahydrofuran (THF)/water mixtures (FIG. 4C). Upon the increase of fw, a significant fluorescence enhancement was observed clearly, whereas no emission was observed in the pure THF solution. The strongest emission intensity at ~950 nm reached its maximum value at 90 vol % water content, which was ~35-fold higher than that in the pure THF due to the restriction of intramolecular rotation (FIG. 5D). TSPCI in aggregate state showed bright emission in a broad NIR-II spectrum range of 1000-1700 nm.

Example 4

In Vivo and Ex Vivo Imaging Study

NIR-I fluorescence imaging was performed using the Maestro in vivo imaging system (CRI, Inc.). To acquire fluorescence of an NIR-I AIEgen (TTD), a 605 nm (+25 nm) bandpass filter and a 645 nm longpass filter were selected as the excitation filter and the emission filter, respectively. NIR-II imaging was performed using the home-built NIR-II in vivo imaging system. The excitation light was provided by an 808 nm diode laser. The emitted light from the TSPCI was filtered through a 1000 nm long-pass filter, which was coupled with a two-dimensional InGaAs array camera (with spectral response range of 900-1700 nm, Photonic Science) for NIR-II fluorescence signal collection. The excitation power density at the imaging plane was 6.4 mW/cm$^2$, much lower than the safe exposure limit of 330 mW/cm$^2$ at 808 nm determined by the International Commission on Nonionizing Radiation Protection. The exposure time for all images was 100 ms.

Figure 5E:
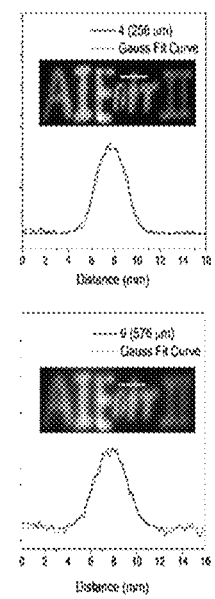
Figure 5F:
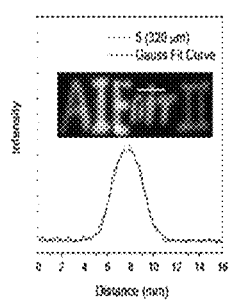
Figure 5G:
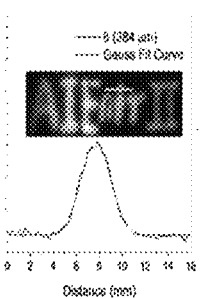
Figure 5H:
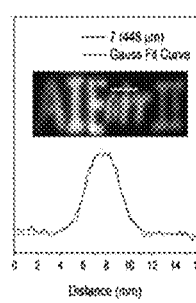
Figure 5I:
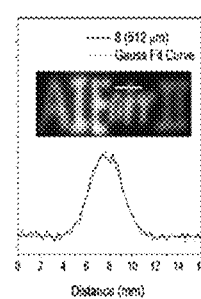
Figure 5J:
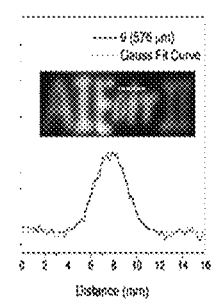

TSCPI was used to draw letters on two panels for imaging. NIR-II fluorescence imaging of the panels uncovered and with different layers of paper covering was then performed using an InGaAs-based NIR-II camera. FIG. 5A depicts the full width at half maximum (FWHM) curve analysis and the corresponding NIR-II fluorescence image (inset) of the TSPCI-drawn panel with no paper layer covering. FIG. 5B depicts the full width at half maximum (FWHM) curve analysis and the corresponding NIR-II fluorescence image (inset) of the TSPCI-drawn panel with one paper layer (64 μm). FIG. 5C depicts the full width at half maximum (FWHM) curve analysis and the corresponding NIR-II fluorescence image (inset) of the TSPCI-drawn panel with two paper layers (128 μm). FIG. 5D depicts the full width at half maximum (FWHM) curve analysis and the corresponding NIR-II fluorescence image (inset) of the TSPCI-drawn panel with three paper layers (192 μm).). FIG. 5E depicts the full width at half maximum (FWHM) curve analysis and the corresponding NIR-II fluorescence image (inset) of the TSPCI-drawn panel with four paper layers (256 μm). FIG. 5F depicts the full width at half maximum (FWHM) curve analysis and the corresponding NIR-II fluorescence image (inset) of the TSPCI-drawn panel with five paper layers (320 μm). FIG. 5G depicts the full width at half maximum (FWHM) curve analysis and the corresponding NIR-II fluorescence image (inset) of the TSPCI-drawn panel with six paper layers (384 μm). FIG. 5H depicts the full width at half maximum (FWHM) curve analysis and the corresponding NIR-II fluorescence image (inset) of the TSPCI-drawn panel with seven paper layers (448 μm). FIG. 5I depicts the full width at half maximum (FWHM) curve analysis and the corresponding NIR-II fluorescence image (inset) of the TSPCI-drawn panel with eight paper layers (512 μm). FIG. 5J depicts the full width at half maximum (FWHM) curve analysis and the corresponding NIR-II fluorescence image (inset) of the TSPCI-drawn panel with nine paper layers (576 μm). FIG. 6 depicts the spatial resolution anlaysis, in order, of each of the NIR-II fluorescence images provided in FIGS. 5A-5J.

TSPCI was added to water under sonication to provide a TSPCI solution. The TSPCI solution was administered to a mouse by intravenous injection. FIG. 7A depicts an NIR-II fluorescence image of the nude mouse before intravenous injection of TSPCI solution. FIG. 7B depicts an NIR-II fluorescence image of the nude mouse one second after injection of TSPCI solution. FIG. 7C depicts an NIR-II fluorescence image of the nude mouse two seconds after injection of TSPCI solution. FIG. 7D depicts an NIR-II fluorescence image of the nude mouse three seconds after injection of TSPCI solution. FIG. 7E depicts an NIR-II fluorescence image of the nude mouse four seconds after injection of TSPCI solution. FIG. 7F depicts an NIR-II fluorescence image of the nude mouse five seconds after injection of TSPCI solution. FIGS. 7A-7F confirmed that TSPCI achieves high contrast and penetration depth for in vivo dynamic NIR-II imaging.

The present subject matter being thus described, it will be apparent that the same may be departure from the spirit and scope of the present subject matter, and all such modifications and modified or varied in many ways. Such modifications and variations are not to be regarded as a variations are intended to be included within the scope of the following claims.

We claim:
1. A compound having a backbone structural formula as follows:

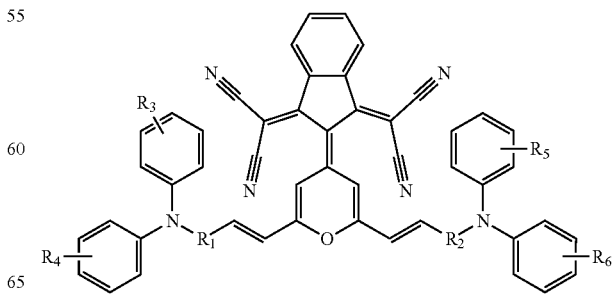

wherein each of $R_1$ and $R_2$ is independently selected from the group consisting of
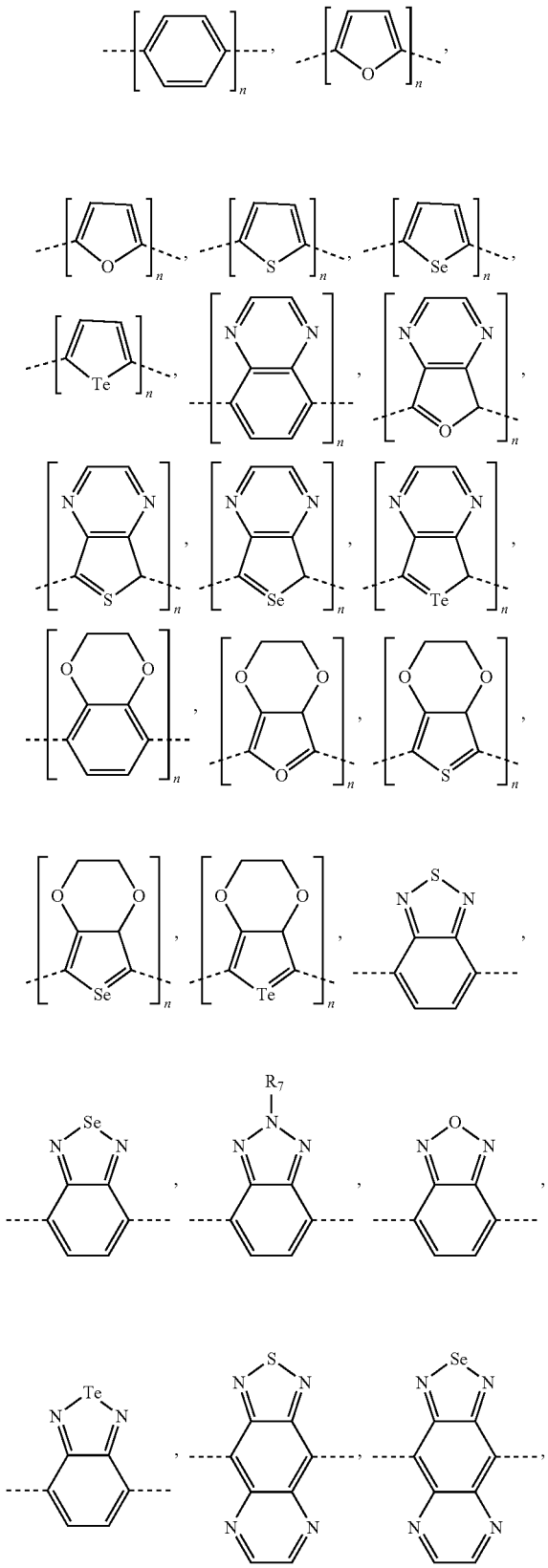
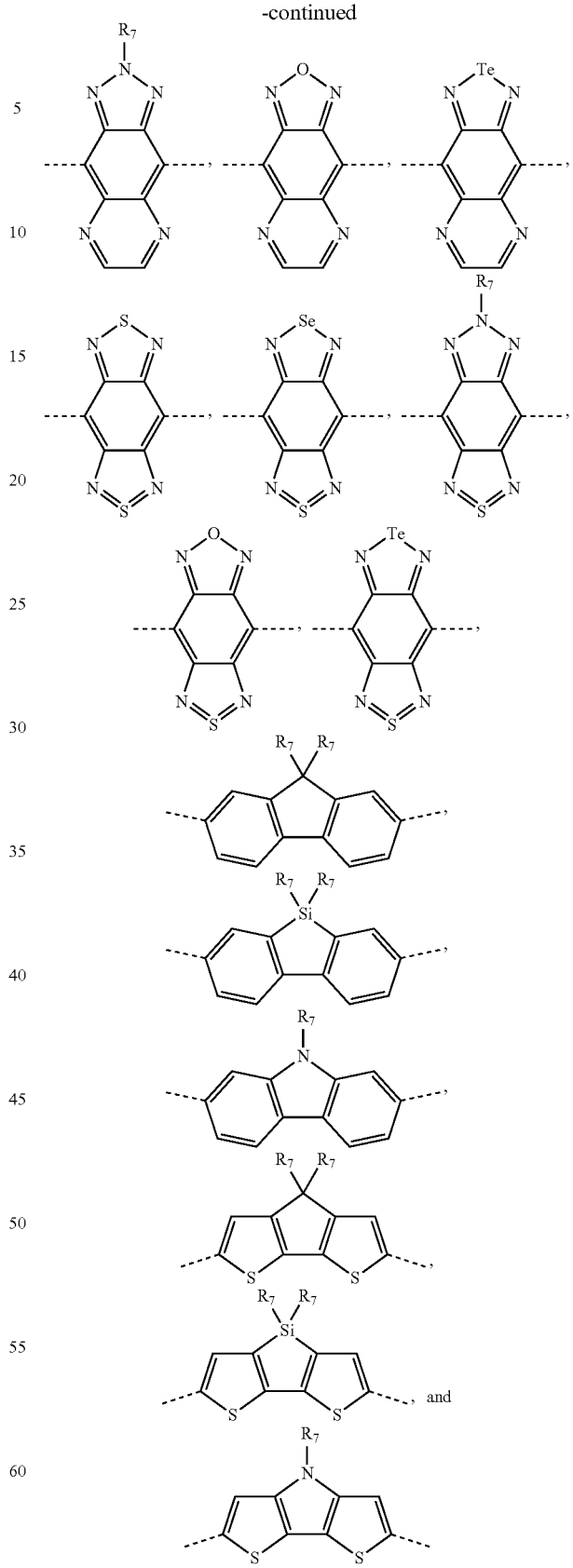
wherein each of $R_3$, $R_4$, $R_5$, and $R_6$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group;

wherein $R_7$ is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, and alkoxy group; and n is an integer selected from 1, 2, 3, 4, and 5.

2. The compound according to claim 1, wherein the compound is:

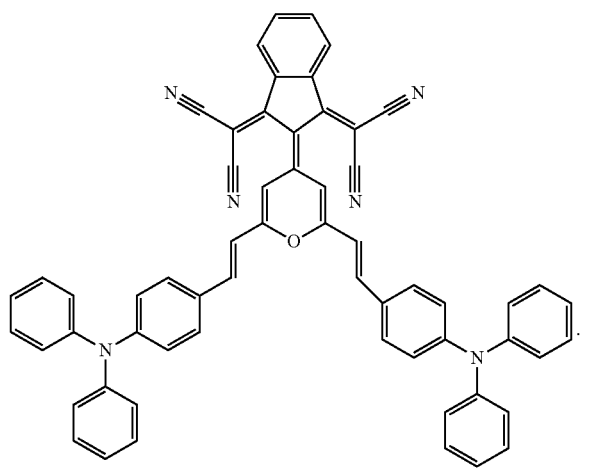 [SMILES: N#CC(C#N)=C1C(=C2C=C(/C=C/c3ccc(N(c4ccccc4)c4ccccc4)cc3)OC(/C=C/c3ccc(N(c4ccccc4)c4ccccc4)cc3)=C2)C(=C(C#N)C#N)c2ccccc21]

3. The compound of claim 1, wherein the compound has a spectral emission range of 1000 nm to 1700 nm.

4. The compound of claim 3, wherein the compound has a spectral emission range of 1000 nm to 1300 nm.

5. The compound of claim 1, wherein the compound has fluorescent properties when in a solid state.

6. The compound of claim 1, wherein the compound comprises a donor group and an acceptor group.

7. A fluorescence imaging method for imaging a target cell, comprising:
contacting a target cell with the compound of claim 1 to obtain a contacted target cell; and
performing fluorescence imaging of the contacted target cell in the near infrared spectral region.

8. A method of cellular imaging comprising:
contacting a target cell with the compound according to claim 1; and
detecting a presence or absence of a target of interest in the target cell using fluorescence imaging in the near infrared range, wherein the target of interest in the target cell comprises at least one of a peptide, a sugar, an aptamer, and an antibody; and wherein a fluorescence emission indicates the presence of the target of interest.

9. The method of claim 8, wherein the target cell is a cancer cell.

10. A method of killing a cancer cell, comprising:
contacting a target cancer cell with the compound according to claim 1;
imaging the target cancer cell while the compound contacts the target cancer cell using fluorescence imaging in the near infrared range; and
irradiating the target cancer cell with light while the compound is contacting the target cancer cell to kill the target cancer cell.

11. A method of synthesizing a fluorescent compound with a twisted quasi-double bond bridging an electron-deficient acceptor and an electron donor, the method comprising:
reacting 1,3-bis(dicyanomethylene)indan with 2,6-dimethyl-4-pyrone to generate and intermediate compound having a structural formula as follows

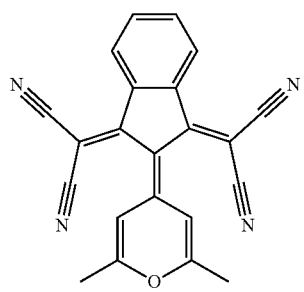

M1 and reacting the intermediate compound with

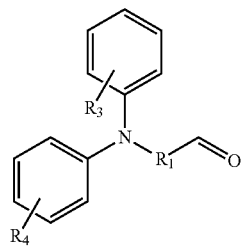

and

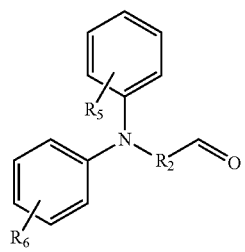

to provide the fluorescent compound of claim 1, wherein $R_1$, $R_2$, $R_3$, $R_4$, $R_5$, and $R_6$ are defined in claim 1.

12. A compound having a structural formula as follows:

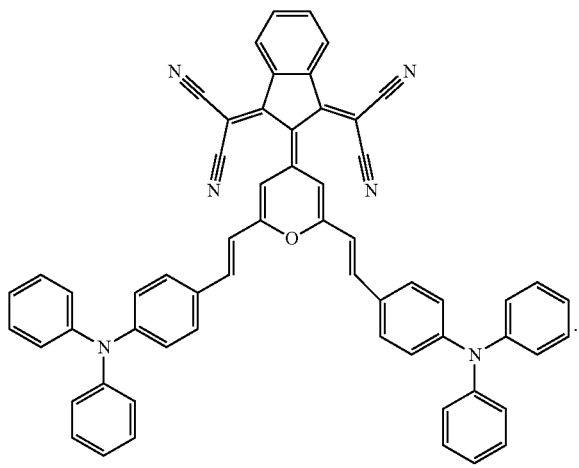 [SMILES: N#CC(C#N)=C1C(=C2C=C(/C=C/c3ccc(N(c4ccccc4)c4ccccc4)cc3)OC(/C=C/c3ccc(N(c4ccccc4)c4ccccc4)cc3)=C2)C(=C(C#N)C#N)c2ccccc21]

13. The compound of claim 12, wherein the compound has a spectral emission range of 900 nm to 1700 nm.

14. The compound of claim 12, wherein the compound has a spectral emission range of 900 nm to 1300 nm.

15. The compound of claim 12, wherein the compound has fluorescent properties when in a solid state.

16. A method of killing a cancer cell, comprising:
contacting a target cancer cell with the compound according to claim 12;
imaging the target cancer cell while the compound contacts the target cancer cell using fluorescence imaging in the near infrared range; and
irradiating the target cancer cell with light while the compound is contacting the target cancer cell to kill the target cancer cell.

17. A fluorescence imaging method for imaging a target cell, comprising:
contacting a target cell with the compound of claim 12 to obtain a contacted target cell; and
performing fluorescence imaging of the contacted target cell in the near infrared spectral region.

18. A method of cellular imaging comprising:
contacting a target cell with the compound according to claim 12; and
detecting a presence or absence of a target of interest in the target cell using fluorescence imaging in the near infrared range, wherein the target of interest in the target cell comprises at least one of a peptide, a sugar, an aptamer, and an antibody; and wherein a fluorescence emission indicates a presence of the target of interest.

* * * * *